(12) United States Patent
Terazaki et al.

(10) Patent No.: US 6,491,957 B2
(45) Date of Patent: Dec. 10, 2002

(54) CHINESE SNACKS

(75) Inventors: Hirofumi Terazaki, Oura-gun (JP);
Masata Mitsuiki, Oura-gun (JP);
Yoshiharu Kinoshita, Oura-gun (JP);
Shinichi Kamiya, Oura-gun (JP);
Syouji Sakaguchi, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 09/892,446

(22) Filed: Jun. 28, 2001

(65) Prior Publication Data

US 2002/0037343 A1 Mar. 28, 2002

(30) Foreign Application Priority Data

Jun. 29, 2000 (JP) ........................................ 2000-196887

(51) Int. Cl.[7] .............................................. A21D 13/00
(52) U.S. Cl. ........................ 426/94; 426/302; 426/496; 426/656
(58) Field of Search .......................... 426/656, 94, 602, 426/289, 496

(56) References Cited

U.S. PATENT DOCUMENTS

| | | | | | |
|---|---|---|---|---|---|
| 5,182,130 | A | * | 1/1993 | Haralampu et al. | 426/302 |
| 5,658,605 | A | * | 8/1997 | Soeda et al. | 426/7 |
| 5,858,423 | A | * | 1/1999 | Yajima et al. | 426/3 |
| 6,270,814 | B1 | * | 8/2001 | Han et al. | 426/36 |

* cited by examiner

*Primary Examiner*—Lien Tran
(74) *Attorney, Agent, or Firm*—Oblon, Spivak, McClelland, Maier & Neustadt, P.C.

(57) ABSTRACT

Chinese snacks having a proteinic adhesive layer with which transglutaminase has reacted, formed between the filling and the dumpling skin thereof are disclosed, and uncooked Chinese snacks half-made in such that a proteinic adhesive layer can be formed between the filling and the dumpling skin thereof by the action of transglutaminase, as well as such Chinese snacks in the frozen form (frozen foods), which undergo a less change in eating texture and have a fresh texture maintained both at the skin portion and filling even for many hours after cooking, after thawing, or the like.

14 Claims, 1 Drawing Sheet

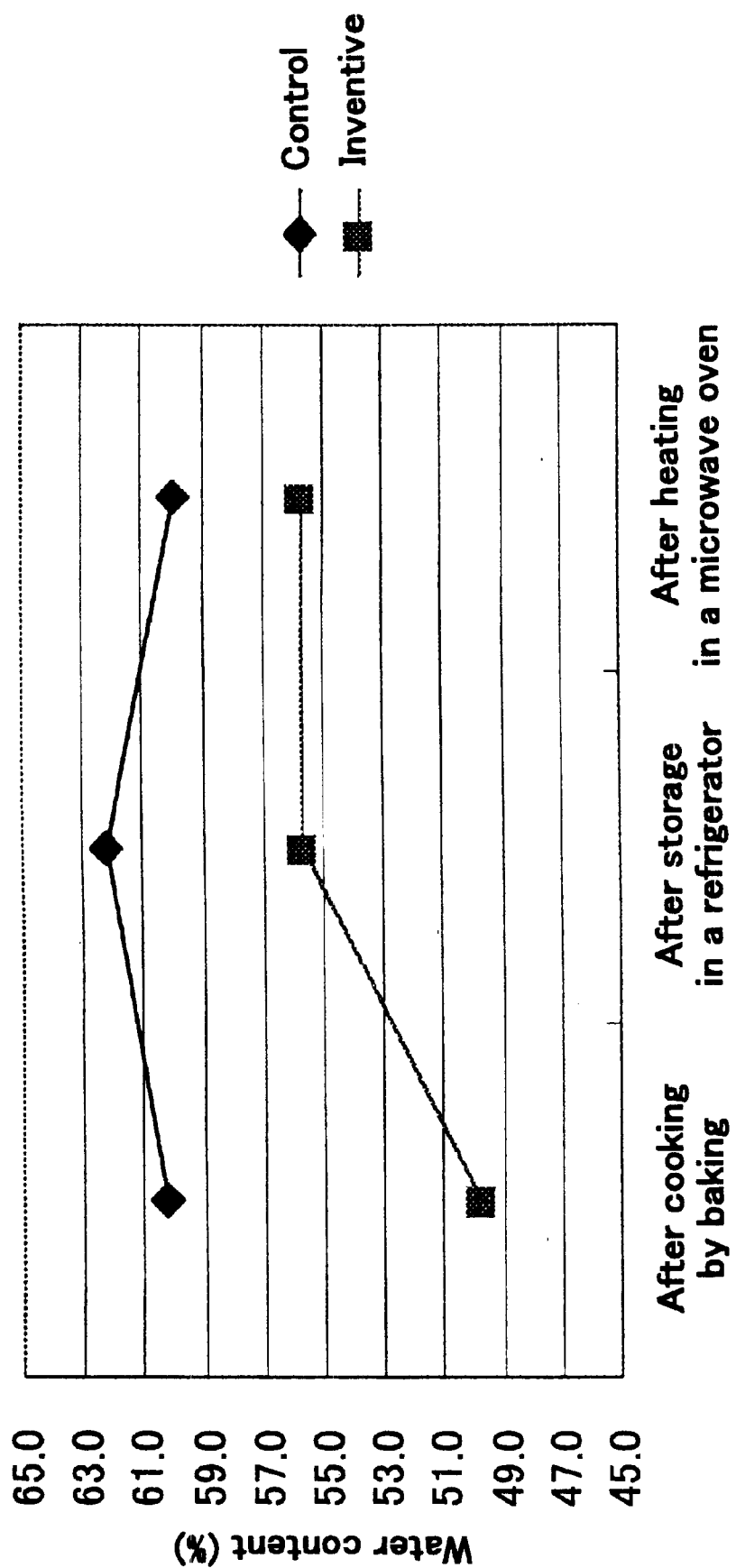
Fig. 1 Change in water content at the skin portion

CHINESE SNACKS

BACKGROUND OF THE INVENTION

Technical Field of the Invention

The present invention relates to Chinese snacks which undergo a less change in eating texture and are capable of maintaining the excellent fresh eating texture. More specifically, the invention pertains to Chinese snacks which are capable of maintaining the fresh eating texture even after heating for cooking, storing in the frozen form, thawing upon selling, storing the thawed product for many hours or re-heating upon eating, by forming, between the filling and the dumpling skin of the snacks, a proteinic adhesive layer with which transglutaminase has reacted. Incidentally, at supermarkets or convenience stores, Chinese snacks which have been delivered thereat in the frozen form, are usually sold after thawing or cooking and then storing at room temperature or in a refrigerator, and purchasers heat them again upon eating. Of course, it is possible for a purchaser to heat the frozen Chinese snacks directly to a temperature suited for eating with a microwave oven or the like.

Prior Art

Many kinds of Chinese snacks require a heating step for making. Chinese snacks in the frozen form which have recently shown a steady increase on the market require, in addition thereto, re-heating in a microwave oven or the like upon thawing (at the stores as described above) or eating.

During such heating (step) or thawing step, or further, during storage after thawing, or the like, however, dripping becomes a problem. This dripping induces, in turn, various problems. Described specifically, dripping is accompanied with outflow of nutrients or components relating to the taste. In addition, since the dumpling skin portion of the Chinese snacks is swollen with water or oils and fats flowing out from their filling, not only eating texture but also their appearance is deteriorated. Moreover, owing to this outflow of water or oils and fats, the filling loses its juicy texture and becomes hard, and crumbling. Such a change in the eating texture and the like caused by dripping at the dumpling skin portion or filling has markedly deteriorated the preference for Chinese snacks. Upon storage at room temperature or in a refrigerator after cooking, or heating in a microwave oven upon eating, water transfer from the filling to the skin portion proceeds, resulting in a further deterioration in appearance and eating texture.

It is the common practice to add extra water or oils and fats to the filling in order to prevent a deterioration in the eating texture of the filling, in other words, to maintain juicy texture of the filling. An increase in the amount of water or oils and fats softens the food, thereby deteriorating moldability or formability. It also causes problems such as an increase in the amount of dripping during a heating step for sterilization or cooking, or during a thawing step for selling, and also an increase in the transfer amount of water from the filling to the skin portion upon storage at room temperature or in a refrigerator or heating in a microwave oven, leading to acceleration of a deterioration in the appearance of the skin portion or eating texture.

Technology has been reported to supplement the juicy texture of the filling by adding thereto a polysaccharide gel (Japanese Patent Application Laid-Open (Kokai) No. Hei 2-145157) or dry mashed potato and/or gellan gum gel (Japanese Patent Application Laid-Open (Kokai) No. Hei 8-317780). Although such techniques bring about some effects for improving the juicy texture of the filling just after cooking, the improved texture does not last long and moreover, the eating texture at the skin portion is, on the contrary, deteriorated by the addition.

Technical developments have so far been conducted for preventing a deterioration in the appearance or eating texture of the skin portion due to the transfer of water and the like from the filling. For example, reported are techniques for reducing the dripping amount from the filling by relaxing thawing conditions of frozen beef (Japanese Patent Application Laid-Open (Kokai) No. Hei 1-181740), spraying a high-temperature oil on the surface of a vegetable, thereby forming its film thereover (Japanese Patent Application Laid-Open (Kokai) No. Hei 2-238860), removing dripping from meat which appears upon heating, by using a water absorptive material (Japanese Patent Application Laid-Open (Kokai) No. Hei 4-211325), or the like. According to these techniques, however, deteriorations in the appearance and eating texture of the skin portion can be suppressed, but they have a difficulty in maintaining the juicy texture of the filling.

A method wherein transglutaminase is used, is also proposed. Described specifically, reported as a method for making transglutaminase react with the surface or skin used for the dumpling skin portion of Chinese snacks are a method wherein transglutaminase is kneaded into noodles (Japanese Patent Application Laid-Open (Kokai) No. Hei 6-14733, Japanese Patent Application Laid-Open (Kokai) No. Hei 6-225717, Japanese Patent Application Laid-Open (Kokai) No. Hei 9-28334, and the like), a method wherein noodles are dipped in a transglutaminase solution (Japanese Patent No. 2749363), a method wherein noodles are dusted or scattered with a powdery transglutaminase preparation (Japanese Patent Application Laid-Open (Kokai) No. Hei 11-9209), and the like. According to the above-described methods, however, noodles are only reacted with by transglutaminase. The methods can be recognized to be slightly effective in preventing swelling of the skin portion, but are not recognized at all to be effective in retaining juicy texture of the filling.

As has been described above, it is very difficult to maintain, for many hours, the fresh appearance and eating texture of the skin portion and also the juicy texture of the filling, and the existing techniques cannot attain this.

SUMMARY OF THE INVENTION

[Problems to be Solved by the Invention]

Based on the background of the above-described prior arts, it is an object of the present invention to provide Chinese snacks which undergo a less change in eating texture and have a fresh texture maintained both at the skin portion and filling even for many hours after cooking, after thawing, or the like.

[Means for Solving the Problems]

With a view to overcoming the above-described problems, the present inventors have carried out an extensive investigation. As a result, it has been found that fresh, juicy texture of Chinese snacks can be maintained even after thawing when they are products frozen after cooking (frozen food), after heating (in a microwave oven) upon eating, or the like, by forming, between the filling and the dumpling skin portion, a proteinic adhesive layer with which transglutaminase has reacted. Based on such findings, the present invention has been completed.

Accordingly, the present invention relates to Chinese snacks having a proteinic adhesive layer with which transglutaminase has reacted, formed between the filling and the dumpling skin thereof, and uncooked Chinese snacks half-made in such that a proteinic adhesive layer can be formed between the filling and the dumpling skin thereof by the action of transglutaminase, as well as such Chinese snacks in the frozen form (frozen foods).

BRIEF DESCRIPTION OF THE DRAWING

FIG. 1 illustrates the comparison between the inventive product and the control product in the transfer of water from the filling to the skin portion (Inspectional Example 1).

DETAILED DESCRIPTION OF THE INVENTION

The present invention will hereinafter be described mare specifically.

No particular limitations are imposed on the Chinese snacks according to the present invention, and as examples thereof may be mentioned Chinese gyoza (a dumpling with minced pork and vegetable stuffing) such as steamed gyoza, baked gyoza or fried gyoza, Chinese spring roll, Chinese Shao-mai (a steamed Chinese pork dumpling wrapped in a thin flour-and-water pancake), and Chinese bun (a bun with a bean-jam or the like filling), each containing as its filling livestock meat such as chicken, pork, beef and the like, various fish and shellfish meats and ground meat thereof, and vegetables such as leek, cabbage, bamboo shoot, mushroom, onion and the like. The skin portion is prepared by adding, to grain flour such as wheat flour, rice flour, starch, or the like, water and other side raw materials, kneading the mixture in a conventional manner and then rolling the kneaded mass. No particular limitations are imposed on the properties and the like thereof insofar as the desired effects of the present invention can be brought about.

Since the Chinese snacks having a proteinic adhesive layer with which transglutaminase has been made to react, formed between the filling and the skin portion thereof, can be prepared in accordance with ordinary manners except that the proteinic adhesive layer with which transglutaminase has been made to react is formed between the filling and the skin portion, the preparation process will next be described while paying a particular attention to this point.

Although any transglutaminase can be used irrespective of its origin, that derived from microorganisms is economically preferred because it is inexpensive. Transglutaminase is used preferably in an amount of 1 to 100 activity units per 1 g of the substrate protein (e.g., in an amount of 0.1 to 10% (weight) relative to the substrate protein in the case of a transglutaminase enzyme preparation having a specific activity of 1,000 units/g), more preferably 2.5 to 20 activity units per 1 g of the protein substrate (e.g., 0.25 to 2.0% in the case of the above-described enzyme preparation). Amounts of transglutaminase smaller than the above-described range do not bring about sufficient effects. Amounts greater than the range, on the other hand, only increase the cost, because effects in proportion thereto are not brought about. The activity unit of an enzyme described above is in accordance with the definition and measuring method described in Japanese Patent Application Laid-Open (Kokai) No. Hei 1-27471.

Preferred examples of proteins with which the enzyme transglutaminase is made to react include casein, salts of casein such as sodium caseinate, soybean protein, muscle protein such as livestock meat, fish meat and the like, collagen, gelatin, egg protein such as hen's egg, and the like, these proteins being rich in reactivity with transglutaminase. The protein is used preferably in an amount of about 0.0001 to about 0.05 g, more preferably about 0.0004 to about 0.003 g per 1 $cm^2$ of the inside surface area of the skin portion of the Chinese snack. Amounts less than the above-described range do not bring about sufficient effects, while amounts greater than the range lead to a proportionate rise in the amount of the enzyme, resulting in cost increase and in addition, they presumably exert a bad influence on the eating texture.

One of the specific methods for forming a proteinic adhesive layer with which transglutaminase has been made to react, between the filling and skin portion by using transglutaminase in predetermined amounts and protein, is, for example, carried out by applying transglutaminase and protein on the surface of the filling formed into a certain shape and/or the inside surface of the skin portion. From the viewpoint of uniform applying, the application onto the inside surface of the skin portion is preferred to that onto the surface of the filling formed into a certain shape. Upon applying, transglutaminase and protein may be applied separately or a formulation or preparation having both mixed therein in advance, may be used. Alternatively, transglutaminase and protein may be mixed in predetermined amounts just before use. No particular limitations are imposed on the applying method of transglutaminase and protein to the skin portion and/or the filling insofar as a proteinic adhesive layer is finally formed between the filling and the skin portion. Preferred examples thereof include powder applying (when a necessary amount of water for exhibition of enzymatic action of transglutaminase is available from the water contained in the filling and/or the skin portion), spraying or applying a solution having the enzyme dissolved therein, and adding by dipping in this solution.

After applying transglutaminase and protein, by, e.g., any one of the above-described methods, onto the skin portion and/or the filling formed into a certain shape, the filling is wrapped with the skin in an ordinary manner. The Chinese snacks thus formed are cooked by heating in an ordinary manner, for example, baking, steaming, boiling, frying or the like.

As is known well, conditions specific to a given enzyme such as pH and temperature must be satisfied for the exhibition of its enzymatic action. According to the present invention, the pH condition is satisfied naturally or spontaneously, i.e., without any extra operation. With regard to the temperature condition, the transglutaminase reacts with the protein, which has been applied together therewith, during the temperature increasing operation for cooking, whereby between the filling and the skin portion, a proteinic adhesive layer for bonding them is formed. This proteinic adhesive layer having a crosslinked structure reinforced by the action of transglutaminase on the layer prevents the transfer of water and oils and fats from the filling to the skin portion, whereby the effects of the present invention can be brought about. As has been described, the occurrence of dripping is prevented in this way during cooking so that the Chinese snacks of the present invention have excellent fresh eating texture, and in addition, this excellent eating texture can be maintained for many hours. In order to attain sufficient effects of the present invention, it is possible to allow the Chinese snacks, which have been formed into a desired shape but not yet cooked, to stand for 30 minutes to overnight at 30° C. or less prior to cooking, whereby the enzymatic reaction of the transglutaminase can be accelerated. This step is, however, not indispensable, because it complicates the preparation process.

The Chinese snacks thus cooked by heating can be distributed not only as chilled foods, but also as frozen foods, because the effects of the present invention is similarly available even when they are frozen in a conventional manner. The present invention makes it possible to markedly alleviate the above-described deteriorations in eating texture and appearance caused during storage of unfrozen Chinese snacks after cooking, by thawing of the frozen desserts, or the like causes.

The Chinese snacks prepared in accordance with the above-described procedure, but half-finished, can be distributed as chilled foods in the uncooked form, that is, after wrapping the filling with the skin portion but prior to cooking by heating or as frozen foods in the uncooked form. Accordingly, the present invention also relates to uncooked Chinese snacks which are prepared to have a proteinic adhesive layer by the action of transglutaminase to be formed between the filling and the skin portion by cooking. Since these Chinese snacks of the present invention have not been cooked yet, purchasers can enjoy them as if they were hand-made ones, by heating upon eating.

EXAMPLES

The present invention will hereinafter be described in further details. It should, however, be borne in mind that the present invention is not limited thereto or thereby.

Example 1

(Gyoza)

A filling for gyoza was prepared in a conventional manner by using, as materials, 12 parts (parts and part meaning part by weight and parts by weight, respectively, in this specification) of minced pork, 19 parts of minced chicken, 4 parts of granular vegetable protein, 7.4 parts of seasonings, 6.4 parts of chopped leek, 45 parts of chopped cabbage and 6.2 parts of chopped onion. On the other hand, a solution having 0.7 parts of table salt dissolved in 26.3 parts of water was poured to 73 parts of wheat flour. They were kneaded with a mixer, followed by rolling roughly the kneaded dough, lapping the two resulting dough sheets one on another, and then rolling the lapped sheets into an integrated sheet in a conventional manner, whereby a dough sheet (skin of gyoza) was prepared. An enzyme formulation ("Activa TG-B powder", ex Ajinomoto Co., Inc., enzymatic activity: 5.0 units/g, that is, 5.4 units/g-sodium caseinate) of transglutaminase containing protein (sodium caseinate) was scattered uniformly in an amount of 2.0 g (0.00095 g/cm$^2$, that is, 0.00088 g-sodium caseinate/cm$^2$) per 21×100 cm of the dough sheet. The filling was then wrapped therein, followed by steaming and then quick freezing, whereby frozen gyoza was prepared (Inventive Product 1). In a similar manner to Example 1 except that water and salad oil were added to the filling as in Control 2 which will be described later, frozen gyoza was prepared (Inventive Product 2).

In a similar manner to Example 1 except that changes were made in enzyme, protein or other materials, as comparative products were prepared frozen gyoza's, more specifically, frozen gyoza with non-use of "Activa TG-B" (Control 1), frozen gyoza with non-use of "Activa TG-B" but having a filling added with water and salad oil (amounts being 3.4 parts and 0.9 part, respectively) (Control 2), frozen gyoza for which "Activa TG-M" (another enzyme preparation of transglutaminase free of any other protein, enzymatic activity: 2.0 units/g, ex Ajinomoto Co., Inc.) was used in an amount of 5.0 g per 21×100 cm (i.e., 0.0024 g/cm$^2$) of a dough sheet in accordance with the method as described in Japanese Patent Application Laid-Open (Kokai) No. Hei 11-9209 referred to above (Control 3), and frozen gyoza with non-use of transglutaminase but added only with chicken egg protein in an amount of 1.85 g per 21×100 cm (i.e., 0.00088 g/cm$^2$) of a dough sheet (Control 4).

After storage of these six kinds, in total, of frozen gyoza for one week in the frozen state, they were thawed by heating on a hot plate. They were then charged in a hermetically sealed container, followed by storing for 15 hours in a refrigerator, they were re-heated in a microwave oven just before eating and subjected to organoleptic evaluation. This evaluation was conducted by a panel of 8 experts. The results of the organoleptic evaluation will be shown below in Table 1.

TABLE 1

| | TG-B ("TG-M" in Control 3) | Egg protein | Water | Salad oil | Juicy texture of filling | Agreeableness of skin portion state | Comprehensive evaluation | Comments |
|---|---|---|---|---|---|---|---|---|
| Control 1 | — | — | — | — | 2.5 | 2.5 | 2.8 | lacks in juicy texture |
| Control 2 | — | — | ○ | ○ | 3.3 | 1.8 | 33 | slightly lacks in texture |
| Control 3 | ○ | — | — | — | 2.8 | 3.0 | 3.0 | lacks in juicy texture |
| Control 4 | — | ○ | — | — | 2.5 | 2.5 | 2.8 | lacks in juicy texture |
| Inventive Product 1 | ○ | — | — | — | 7.3 | 8.3 | 7.3 | have a juicy texture |
| Inventive Product 2 | ○ | — | ○ | ○ | 8.5 | 7.8 | 8.5 | have a juicy texture |

(○: used, and —: not used. Juicy texture of filling, Agreeableness of the skin portion state and Comprehensive evaluation: each, an average of scores given by 8 experts based on the 10-stage ranking system from 1 to 10)

As is apparent from the above-described results, the frozen gyoza's as Control 1 and Control 4 lacked in juicy texture because the water content in the filling was absorbed by the dough sheet (skin portion), while the frozen gyoza as Control 2 was slightly improved in the juicy texture by the addition of water and salad oil, but was not recognized to have a juicy texture. Moreover, marked swelling occurred at the skin portion so that both the eating texture and appearance were rated low. The frozen gyoza as Control 3 was a little more improved in swelling of the skin portion than those Controls 1, 2 and 4, but the filling was not recognized to have a juicy texture. Thus, it has been proved that eating-texture-maintaining effects of the prior art were unsatisfactory both at the skin portion and filling.

It has been confirmed, on the other hand, that the inventive products 1 and 2 falling within the scope of the present invention were markedly superior in juicy texture and in the state of the skin portion to any one of Controls 1 to 4 which were comparative products. Concerning these inventive products, adhesion between the filling and the skin was secured, different from the control products, suggesting that the transglutaminase has reacted with the protein used together therewith. This also imparts the product with a substantial feeling, one of the judging items for evaluation of a product quality other than those for juicy texture or eating texture of the skin.

Inspectional Example 1

Among the gyoza's subjected to the above-described organoleptic evaluation (these gyoza's having been cooked by steaming as described in Example 1), the frozen products (frozen foods) of Control 1 and Inventive Product 1 were thawed by heating after storage under the frozen state. The water content thereof after baking until they became brown (cooking by baking), that after storing in a refrigerator, and that after heating in a microwave oven (heating in microwave oven) just before eating were each determined from the drying loss after heating at 105° C. for 21 hours and the transfer of water from the filling to the skin portion was confirmed.

Results will be shown below in FIG. 1. As is apparent from FIG. 1, the transfer of water of the inventive product was prevented each at cooking by baking, storage in a refrigerator and heating in a microwave oven.

It has therefore been confirmed, in addition to the above-described results of organoleptic evaluation, that the inventive products are able to maintain appearance and eating texture of the skin portion for many hours while maintaining the juicy texture of the filling during cooking, after thawing and/or upon storage during cooking or thawing, or thereafter, because of suppression of the transfer of water from the filling to the skin portion.

[Effects of the Invention]

According to the present invention, (frozen) Chinese snacks such as (frozen) gyoza, (frozen) spring roll and the like, can be easily provided, which can maintain fresh, juicy texture even after cooking by heating, thawing by heating or natural thawing, or even by re-heating in a microwave oven, many hours after cooking or thawing.

What is claimed is:

1. A Chinese snack, comprising:
   a filling;
   a dumpling skin surrounding said filling and having an inside surface that faces said filling; and
   a crosslinked proteinic adhesive disposed between said filling and said dumpling skin, which is in contact with said filling and said inner surface and which adheres said filling to said inner surface by a crosslinking reaction between one or more proteins and transglutaminase;
   wherein said crosslinking reaction comprises an enzymatic reaction of transglutaminase on one or more proteins on said filling and one or more proteins on said inside surface of the dumpling.

2. The Chinese snack as claimed in claim 1, wherein said proteinic adhesive comprises a crosslinked enzymatic reaction product of transglutaminase and at least one protein selected from the group consisting of casein, casein salts, sodium caseinate, soybean protein, muscle protein, livestock meat, fish meat, collagen, gelatin, and hen's egg protein.

3. The Chinese snack as claimed in claim 1, wherein said crosslinking reaction comprises an enzymatic reaction between at least one protein on said filling and at least one protein on said inside surface of the dumpling, wherein the protein is present in an amount of about 0.0001 to about 0.05 g per 1 $cm^2$ of the surface area of said inside surface of the dumpling.

4. The Chinese snack as claimed in claim 1, wherein said crosslinking reaction comprises an enzymatic reaction between at least one protein on said filling and at least one protein on said inside surface of the dumpling, wherein the transglutaminase is present in an amount of 1 to 100 activity units per 1 g of the protein.

5. The Chinese snack as claimed in claim 1, wherein said Chinese snack is selected from the group consisting of Chinese gyoza, steamed gyoza, baked gyoza, fried gyoza, Chinese spring roll, Chinese Shao-mai, and Chinese bun.

6. The Chinese snack as claimed in claim 1, wherein said filling is selected from the group consisting of livestock meat, chicken, pork, beef, fish, shellfish, ground meat, vegetables, leek, cabbage, bamboo shoot, mushroom, and onion.

7. The Chinese snack as claimed in claim 1, which is in a frozen form.

8. An uncooked Chinese snack, comprising:
   a filling;
   a dumpling skin surrounding said filling and having an inside surface that faces said filling; and
   an uncrosslinked proteinic adhesive disposed between said filling and said dumpling skin, which is in contact with said filling and said inner surface and which comprises one or more proteins and transglutaminase and is capable of adhering said filling to said inner surface by a crosslinking reaction between said proteins and said transglutaminase upon cooking;
   wherein said crosslinking reaction comprises an enzymatic reaction of transglutaminase on one or more proteins on said filling and one or more proteins on said inside surface of the dumpling.

9. The uncooked Chinese snack of claim 8, wherein said proteinic adhesive comprises a crosslinked enzymatic reaction product of transglutaminase and at least one protein selected from the group consisting of casein, casein salts, sodium caseinate, soybean protein, muscle protein, livestock meat, fish meat, collagen, gelatin, and hen's egg protein.

10. The uncooked Chinese snack of claim 8, wherein said crosslinking reaction comprises an enzymatic reaction between at least one protein on said filling and at least one protein on said inside surface of the dumpling, wherein the protein is present in an amount of about 0.0001 to about 0.05 g per 1 $cm^2$ of the surface area of said inside surface of the dumpling.

11. The uncooked Chinese snack of claim 8, wherein said crosslinking reaction comprises an enzymatic reaction between at least one protein on said filling and at least one protein on said inside surface of the dumpling, wherein the transglutaminase is present in an amount of 1 to 100 activity units per 1 g of the protein.

12. The uncooked Chinese snack of claim 8, wherein said Chinese snack is selected from the group consisting of Chinese gyoza, steamed gyoza, baked gyoza, fried gyoza, Chinese spring roll, Chinese Shao-mai, and Chinese bun.

13. The uncooked Chinese snack of claim 8, wherein said filling is selected from the group consisting of livestock meat, chicken, pork, beef, fish, shellfish, ground meat, vegetables, leek, cabbage, bamboo shoot, mushroom, and onion.

14. The uncooked Chinese snack of claim 8, which is in a frozen form.

* * * * *